(12) United States Patent
Martínez Escribano et al.

(10) Patent No.: US 12,402,612 B2
(45) Date of Patent: Sep. 2, 2025

(54) CONTAINER FOR TRANSPORTING AND INOCULATING PUPAE

(71) Applicant: ALTERNATIVE GENE EXPRESSION S.L., Madrid (ES)

(72) Inventors: José Ángel Martínez Escribano, Madrid (ES); Miguel Cid Fernandez, Madrid (ES); Edel Reytor Saavedra, Madrid (ES); Carmen Alvarado Fradua, Madrid (ES); Romy Moreno Dalton, Madrid (ES)

(73) Assignee: ALTERNATIVE GENE EXPRESSION S.L., Madrid (ES)

( * ) Notice: Subject to any disclaimer, the term of this patent is extended or adjusted under 35 U.S.C. 154(b) by 72 days.

(21) Appl. No.: 17/632,970

(22) PCT Filed: Jul. 3, 2020

(86) PCT No.: PCT/EP2020/068777
§ 371 (c)(1),
(2) Date: Feb. 4, 2022

(87) PCT Pub. No.: WO2021/023446
PCT Pub. Date: Feb. 11, 2021

(65) Prior Publication Data
US 2022/0287284 A1 Sep. 15, 2022

(30) Foreign Application Priority Data
Aug. 6, 2019 (EP) ..................................... 19382690

(51) Int. Cl.
*A01K 67/30* (2025.01)
*B65D 1/36* (2006.01)
(Continued)

(52) U.S. Cl.
CPC ................ *A01K 67/30* (2025.01); *B65D 1/36* (2013.01); *B65D 21/0209* (2013.01);
(Continued)

(58) Field of Classification Search
CPC .... A01K 67/033; B65D 1/36; B65D 21/0209; B65D 43/0204; B65D 81/263;
(Continued)

(56) References Cited

U.S. PATENT DOCUMENTS 3,750,625 A * 8/1973 Edwards ............... A01K 67/033
119/6.6
3,769,936 A * 11/1973 Swanson ............... A01K 67/033
215/310

(Continued)

FOREIGN PATENT DOCUMENTS

| CA | 2 399 521 A1 | 2/2004 |
|---|---|---|
| CN | 205441242 U | 8/2016 |

(Continued)

OTHER PUBLICATIONS

Triangles the Strongest Shape; Science Made Fun (https://sciencemadefun.net/blog/triangles-the-strongest-shape/) (Year: 2020).*
(Continued)

*Primary Examiner* — Monica L Perry
*Assistant Examiner* — Maria E Graber
(74) *Attorney, Agent, or Firm* — Seed Intellectual Property Law Group LLP

(57) ABSTRACT

The invention refers to a container (1) that can be used for storing, transporting and for inoculating silk-free pupae. The container (1) includes a tray (2) having a flat surface (5) and a plurality of wells (4) formed on the surface (5), wherein each well (4) is configured for accommodating a pupa (8). The container (1) also includes a lid (3) having a plurality of openings (6), wherein the tray (2) and the lid (3) are
(Continued)

configured to be coupled to each other, such that the lid (3) is placed on the flat surface (5), at least partially, closing the wells (4). The wells (4) and the openings (6) are arranged, such that when the tray (2) and the lid (3) are coupled together, each well (4) is accessible through one of the plurality of openings (6). The container is stackable for an optimum and cost-efficient secure transportation.

14 Claims, 10 Drawing Sheets

(51) Int. Cl.
  *B65D 21/02* (2006.01)
  *B65D 43/02* (2006.01)
  *B65D 81/26* (2006.01)
(52) U.S. Cl.
  CPC ........ *B65D 43/0204* (2013.01); *B65D 81/263* (2013.01); *B65D 2203/10* (2013.01); *B65D 2543/00194* (2013.01); *B65D 2543/00703* (2013.01); *B65D 2543/00814* (2013.01)
(58) Field of Classification Search
  CPC ...... B65D 2203/10; B65D 2543/00194; B65D 2543/00703; B65D 2543/00814
  USPC .......................................................... 119/6.5
  See application file for complete search history.

(56) References Cited

U.S. PATENT DOCUMENTS

| | | | |
|---|---|---|---|
| 4,212,267 A * | 7/1980 | Patterson | A01K 1/031 119/6.5 |
| 4,216,763 A * | 8/1980 | Miklas | A47J 37/0664 220/4.24 |
| 4,418,647 A * | 12/1983 | Hoffman | A01K 67/033 119/6.6 |
| 4,646,683 A * | 3/1987 | Maedgen, Jr. | A01K 67/033 119/6.5 |
| 4,711,356 A * | 12/1987 | Dunden | B65D 21/0209 220/23.6 |
| D315,208 S * | 3/1991 | Valencia | D24/224 |
| 5,178,094 A * | 1/1993 | Carr | A01K 67/033 119/6.5 |
| 6,284,531 B1 * | 9/2001 | Zhu | C12M 23/34 435/297.5 |
| 6,474,259 B1 * | 11/2002 | Gaugler | A01K 67/033 119/6.7 |
| 6,517,856 B1 * | 2/2003 | Roe | G01N 33/5085 43/132.1 |
| 6,688,255 B2 * | 2/2004 | Donaldson | A01K 67/033 119/6.5 |
| 6,969,606 B2 * | 11/2005 | Minton | C12M 23/46 435/305.3 |
| 8,143,053 B2 * | 3/2012 | Yerbic | C12M 23/22 435/297.5 |
| 9,469,458 B2 * | 10/2016 | Padda | B65D 43/16 |
| 9,629,339 B2 * | 4/2017 | Newton | A01K 5/00 |
| D841,898 S * | 2/2019 | Selby | A01K 67/033 D30/120 |
| 10,253,288 B2 * | 4/2019 | Müller | C12M 23/38 |
| 10,334,830 B2 * | 7/2019 | Demetrescu | B01F 31/20 |
| 10,405,528 B2 * | 9/2019 | Comparat | B65G 1/0407 |
| 10,687,521 B2 * | 6/2020 | Calis | A01K 67/033 |
| 11,278,014 B2 * | 3/2022 | Martínez Escribano | C12N 15/86 |
| 11,395,474 B2 * | 7/2022 | Hall | A01K 67/033 |
| 11,453,850 B2 * | 9/2022 | Wood | B65D 41/06 |
| 2008/0295774 A1 * | 12/2008 | Van Beek | A01K 67/033 119/6.6 |
| 2010/0102967 A1 * | 4/2010 | Lee | B65D 51/245 340/572.8 |
| 2015/0375898 A1 * | 12/2015 | Matsuda | B65D 21/045 206/449 |
| 2017/0265443 A1 * | 9/2017 | Winston, III | A01M 1/023 |
| 2018/0064143 A1 * | 3/2018 | Klann | A23B 7/148 |
| 2019/0133096 A1 * | 5/2019 | Li | A01K 67/033 |
| 2020/0128797 A1 * | 4/2020 | Curry | A01G 33/00 |
| 2020/0160008 A1 * | 5/2020 | Bok | G06K 7/10445 |
| 2020/0296920 A1 * | 9/2020 | Behling | A01K 67/033 |
| 2022/0295737 A1 * | 9/2022 | Schmitt | A01K 1/0047 |
| 2022/0304290 A1 * | 9/2022 | De Gelder | B65D 85/50 |
| 2023/0137385 A1 * | 5/2023 | Dunn | A01K 67/033 119/322 |
| 2023/0363364 A1 * | 11/2023 | Renoux | A01K 67/0339 |

FOREIGN PATENT DOCUMENTS

| | | | |
|---|---|---|---|
| CN | 208113813 U | * | 11/2018 |
| JP | 2019505178 A | | 2/2019 |
| KR | 20-0207282 Y1 | | 12/2000 |
| WO | 2012/115959 A2 | | 8/2012 |
| WO | 2014/171829 A1 | | 10/2014 |
| WO | 2017/046415 A2 | | 3/2017 |

OTHER PUBLICATIONS

Injection of *Galleria mellonella* Larvae (https://www.frontiersin.org/journals/cellular-and-infection-microbiology/articles/10.3389/fcimb.2017.00099/full) (Year: 2017).*

U.S. Appl. No. 17/632,980, filed Feb. 4, 2022.

* cited by examiner

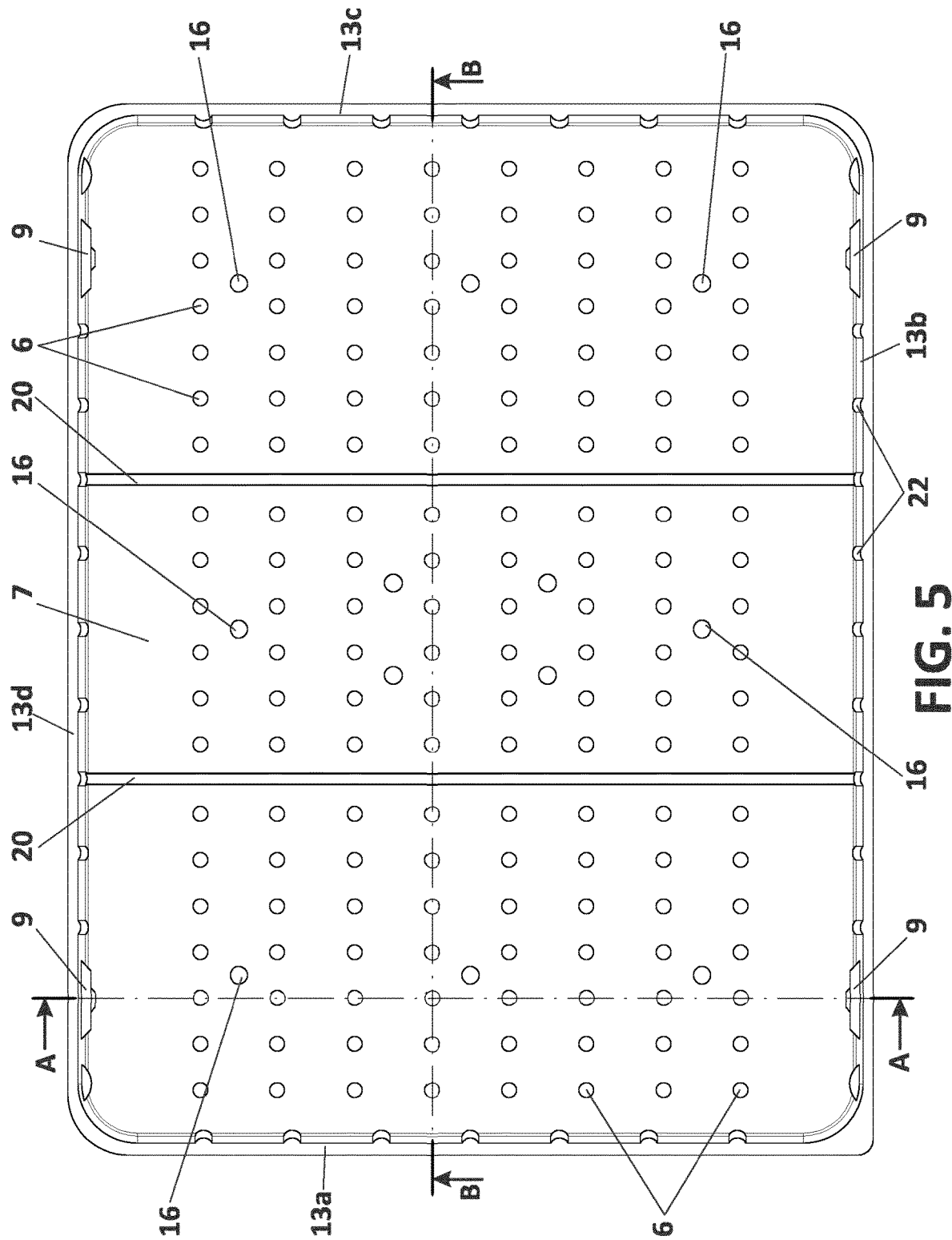

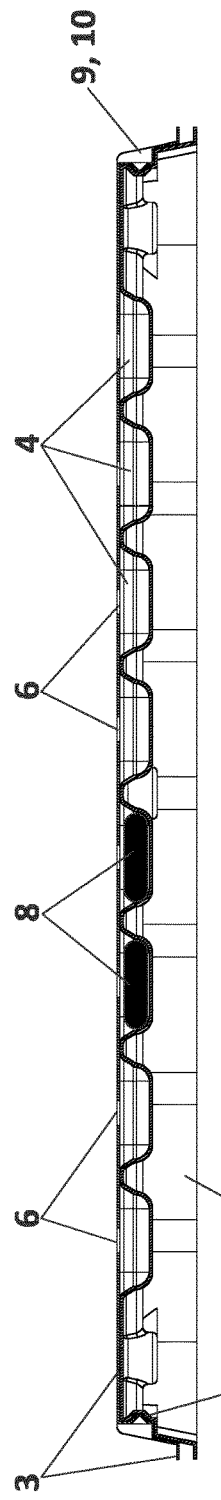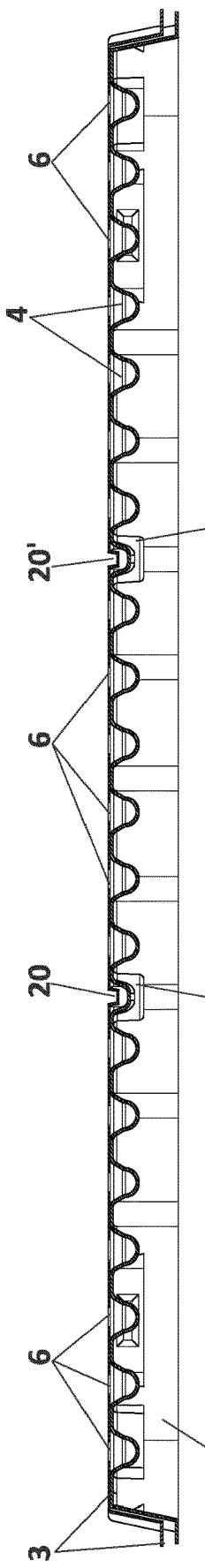

CONTAINER FOR TRANSPORTING AND INOCULATING PUPAE

FIELD AND OBJECT OF THE INVENTION

The present invention refers in general to containers for storing and transporting living insects.

An object of the invention is to provide a multi-purpose container that can be used for storing, transporting and for inoculating insects, especially silk-free pupae, preferably for the automatized industrial production of recombinant proteins from infected insect pupae.

The container object of the invention is stackable for an optimum, cost-efficient and secure transportation, ensuring at the same time that the pupae are exposed to a proper environment in terms of temperature and humidity during storage and transportation.

Additionally, the container object of the invention is disposable and can be manufactured in large numbers at low cost.

BACKGROUND OF THE INVENTION

It is known to use larvae as living biofactories for the expression of recombinant proteins, for example for producing: vaccines, therapeutic molecules or diagnostic reagents.

For example, the PCT publication WO 2017/046415 describes means and methods to optimize the industrial production of recombinant proteins in insect pupae. In the method described in this PCT publication, insect larvae are massively grown in rearing modules until they are transformed in a pupa covered by a silk cocoon. The pupae are subjected to a silk removal process by immersing or spraying the cocoons with a dissolving solution, after which the silk-free pupae are washed to remove traces of the dissolving solution.

After drying the pupae, the silk-free pupae are ready to be inoculated with a recombinant virus vector, or to be stored refrigerated (e.g. at 4° C.) for later use. Typically, the pupae are package and shipped (refrigerated) to an industrial production laboratory, where they are inoculated (infected) to obtain a purified recombinant protein from infected pupae after an incubation period.

For inoculating the pupae, the pupae are arranged in a matrix or array of alveolus, and a robot provided with one or more needles inject a predefined amount of solution containing a virus vector into each pupa, and since the pupae are arranged in a matrix or array, programming of the robot is simple.

The processes of transportation and storage of the pupae before and after inoculation with the vector is complex since they are a fragile living organism and their stock piling may affect their viability or their productivity as living bioreactors. In the previous state of the art, the insect pupae were allocated manually in a re-usable plastic matrix. This methodology is time consuming and cannot be atomized. Additionally, the use of re-usable plastic matrixes may cause cross contaminations when different vectors are used to produce different products in the same inoculation machine.

For the optimization of industrial production of recombinant proteins in an automatized process, efficient transportation and handling of the pupae are essential parts of the process.

SUMMARY OF THE INVENTION

The invention is defined in the attached independent claim, and satisfactorily solves the shortcomings of the prior art, by providing a container that is stackable and that can be used for storing, transporting and for inoculating pupae in a fully automatized process avoiding manual handling of the same.

Therefore, an aspect of the invention refers to a container for transporting and inoculating pupae, that comprises a tray having a substantially flat surface and a plurality of wells formed on the surface, wherein each well is configured for accommodating a pupa. The container also includes a lid for closing at least partially, the wells, wherein the tray and the lid are configured to be coupled to each other, in such a way that the lid is placed on the flat surface of the tray retaining the pupae enclosed in the wells.

The lid as a plurality of openings arranged in correspondence with the positions of the wells, so when the lid and the tray are coupled together, the openings are individually placed over the wells and each well is accessible through an opening. The openings are smaller, in terms of area, than the wells, thus, a silk-free pupa received in a well cannot pass through the opening, that is, the pupa is retained inside the well where it is placed.

The wells and openings are distributed in a regular arrangement, preferably the wells and the openings are distributed in columns and rows configuring an orthogonal matrix.

Furthermore, the tray and the lid are provided with interlocking means to securely retain the tray and the lid engaged during all stages of the process, namely: storage, transportation, inoculation and incubation. Preferably, the interlocking means are integrally formed in the tray and the lid and are configured to mechanically engage tray and lid, in such a manner that the lid overlaps with the flat surface of the tray.

The container is configured to be stackable so two or more containers can be stacked on top of each other, forming a pile of containers, that in turn are packaged in a common container, preferably a refrigerated container. This stackable feature of the containers is very convenient for optimizing the use of a space for storing and shipping the containers.

Two or more containers can be stacked by inserting a top part of a container from below at least partially in the tray of another container. Preferably, the tray is formed by a base defining the flat surface and having four sides and a lateral wall transversally projecting from the base, and extending along the four sides of the base.

Similarly, the lid has a base having four sides and a lateral wall transversally projecting from the base and extending along the four sides of the base. The tray and the lid are configured such as when they are coupled, their bases and lateral walls, at least partially, overlap.

Preferably, the tray and the lid have frusto-pyramidal configuration in order to facilitate stacking two containers, by inserting a top part of a container from below at least partially in the tray of another container.

An air chamber is formed between each pair of consecutive stacked containers to fluidly communicate the wells of the same tray. Additionally, the containers are configured to define ventilation passageways between stacked trays, communicating the air chambers with the exterior environment, so all the wells are fluidly communicated with the exterior environment for proper ventilation, for example inside a controlled environment in terms of temperature and humidity suitable for preserving the pupae in optimum conditions.

These ventilation passageways are formed as overlapping ventilation openings formed in the bases of the lid and tray of each container, so when a lid and tray are coupled, these ventilation openings overlap allowing air to flow through the air chambers and the exterior.

Additionally, ventilation passageways are also provided laterally at the stacked containers, in the form of a cavity or separation between the lateral walls of each pair of stacked containers.

In a preferred embodiment, the container incorporates an information code having information for tracking the container and/or for inoculating the pupae. This information code is an electronically, electromagnetically or optically readable code, that can be read by an inoculation robot. Preferably, the container has a Radio-frequency Identification (RFID) tag containing the information code.

Therefore, the container is compatible with an inoculation robot because there is no need to manually introduce in the robot instructions data for inoculating the pupae.

The invention also refers to a set of stacked containers as the one described above, wherein ventilation passageways are formed laterally between any two consecutive stacked containers, and ventilation passageways that communicate the air chambers are formed by a pair of consecutive stacked containers.

The invention also refers to a temperature and/or humidity controlled package comprising two of more the above-described containers stacked together and placed inside the package, wherein preservation air inside the package reaches each papa through the ventilation passageways.

BRIEF DESCRIPTION OF THE DRAWINGS

Preferred embodiments of the invention are henceforth described with reference to the accompanying drawings, wherein:

FIG. 5—shows a top plan view of the lid and tray coupled together.

FIG. 6—shows a cross-sectional elevational view taken at plane A-A in FIG. 5.

FIG. 7—shows a cross-sectional elevational view along plane B-B in FIG. 5.

PREFERRED EMBODIMENT OF THE INVENTION

Figure 1:
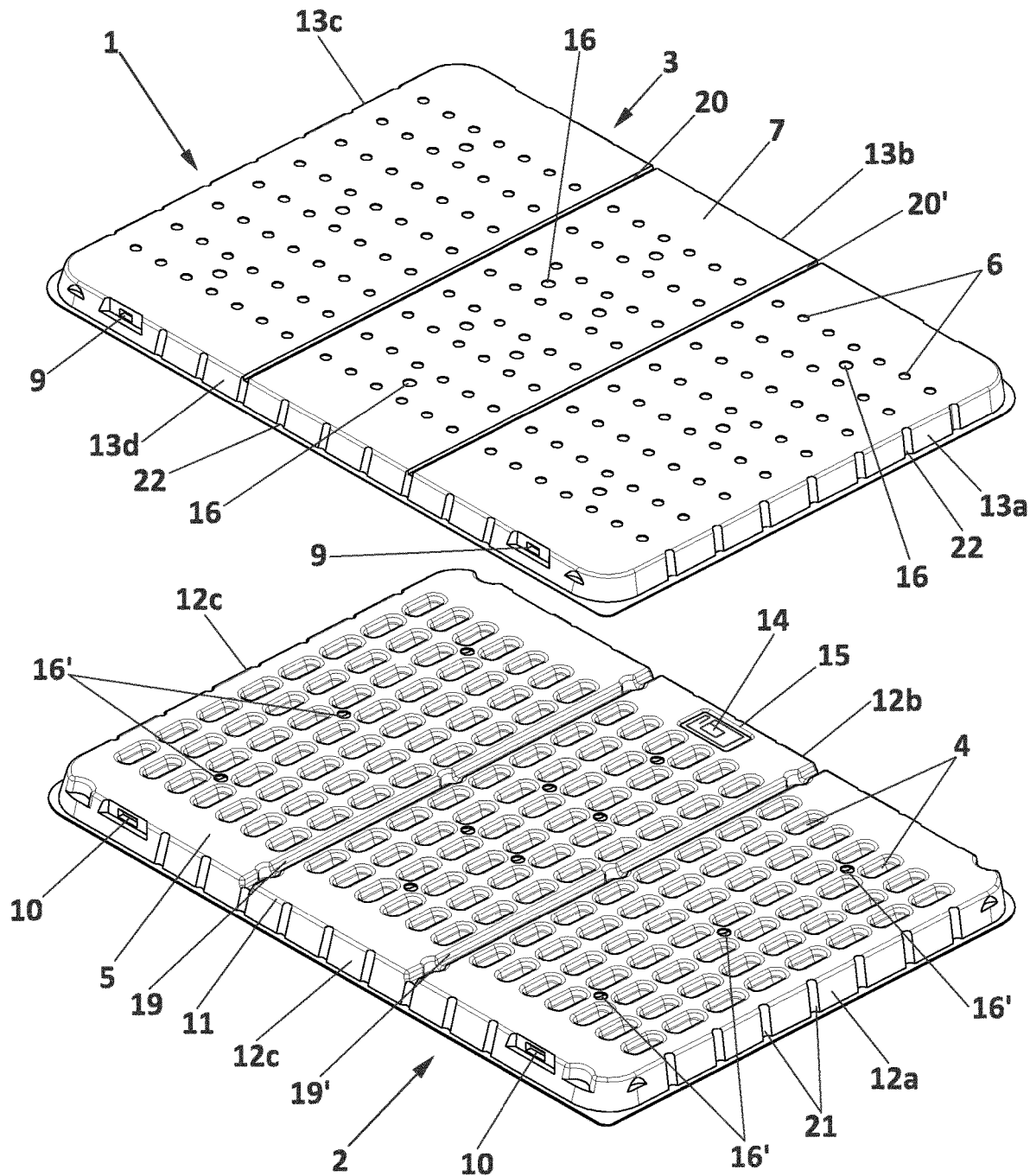
FIG. 1—shows a perspective view from above of a preferred embodiment of the container of the invention, wherein the tray an lid are shown uncoupled.
Figure 2:
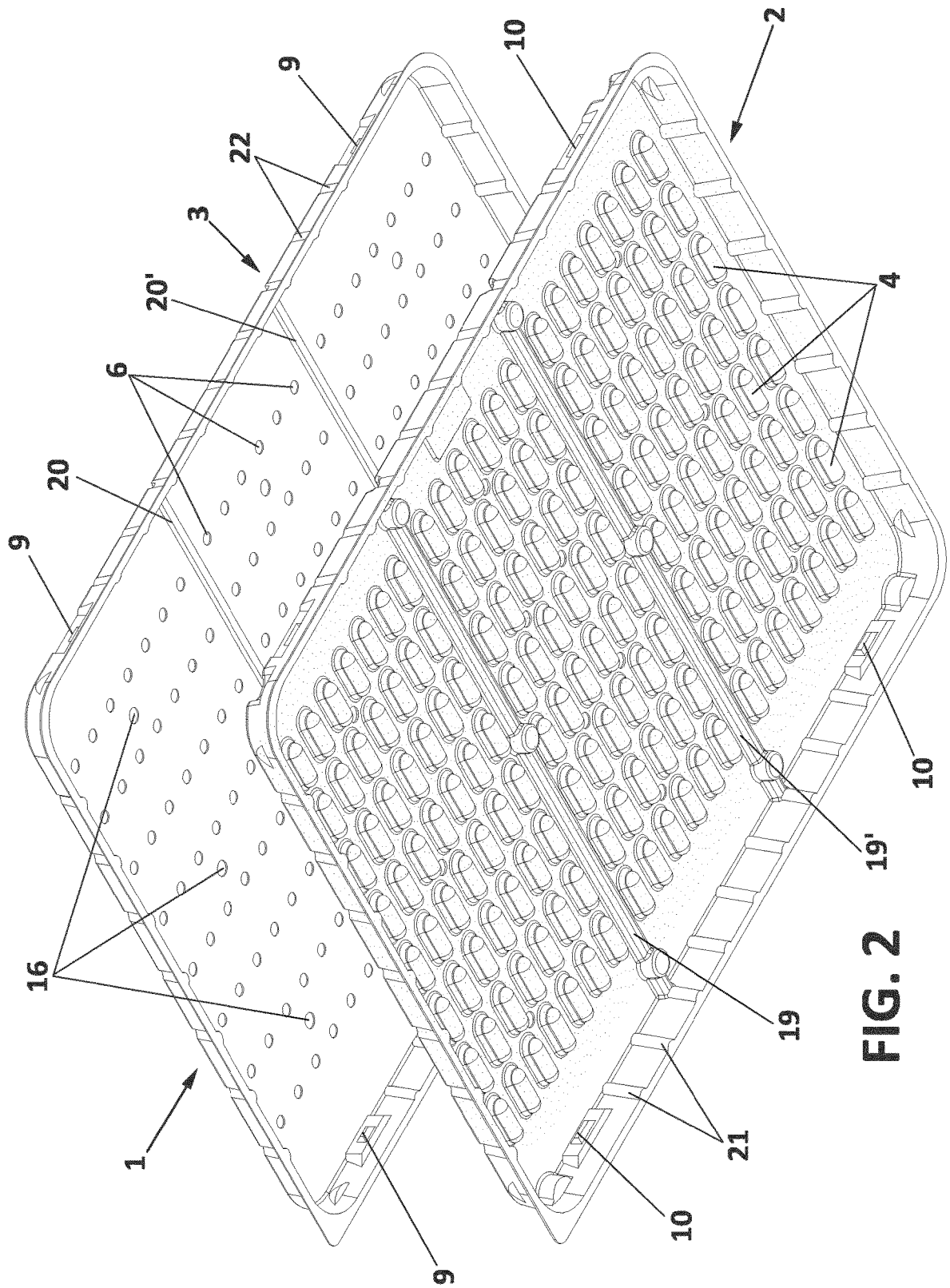
FIG. 2—shows a perspective view from below of the same embodiment of FIG. 1.
Figure 3:
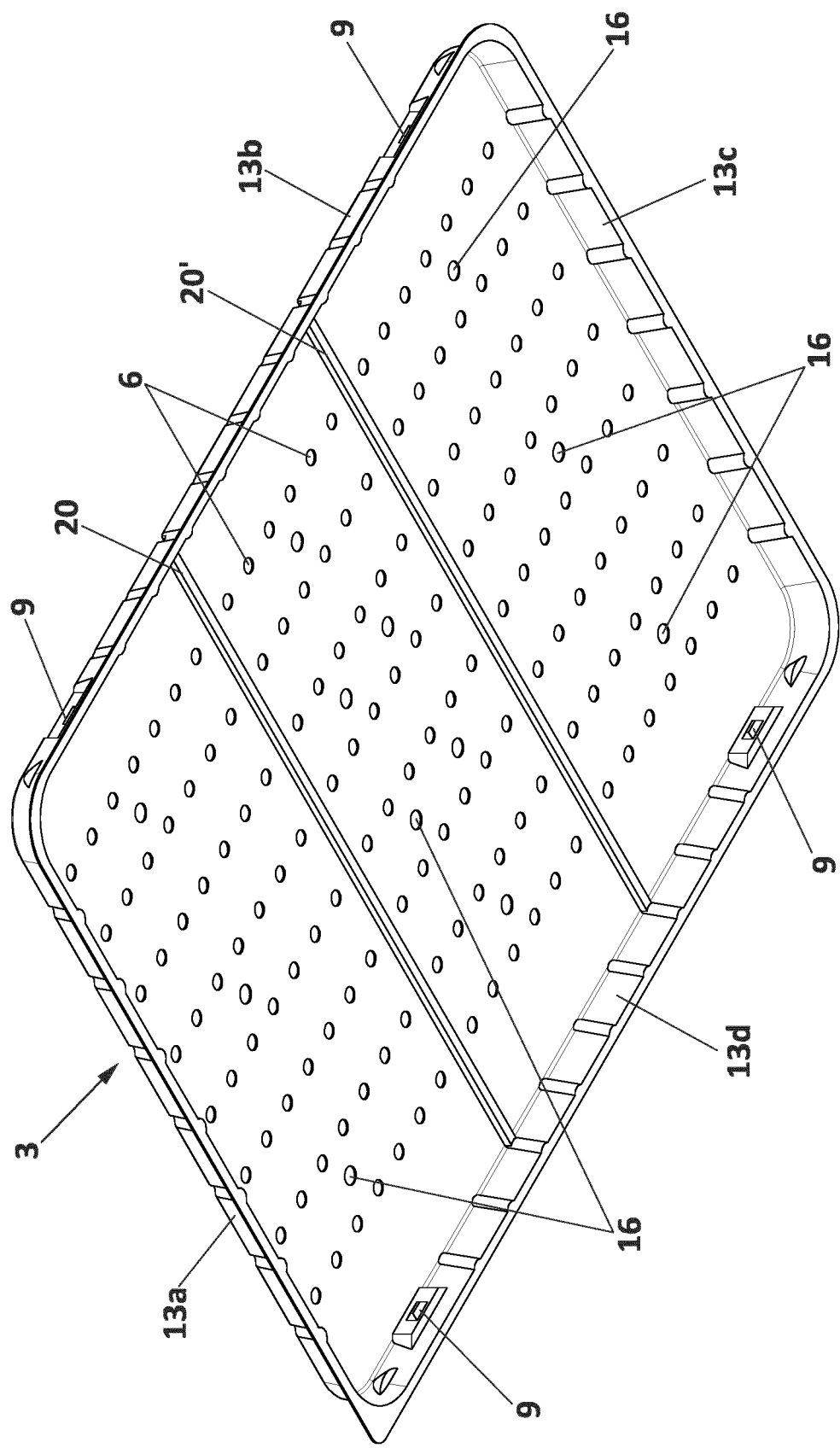
FIG. 3—shows a perspective view from below of the lid.

As shown in FIG. 1, a container (1) according to the invention comprises a tray (2) and a lid (3) that can be coupled to each other for storing and transporting pupae. The tray (2) has flat surface (5) and a plurality of wells (4) formed on the surface (5) wherein each well (4) is configured for receiving and retaining a pupa.

Figure 10:
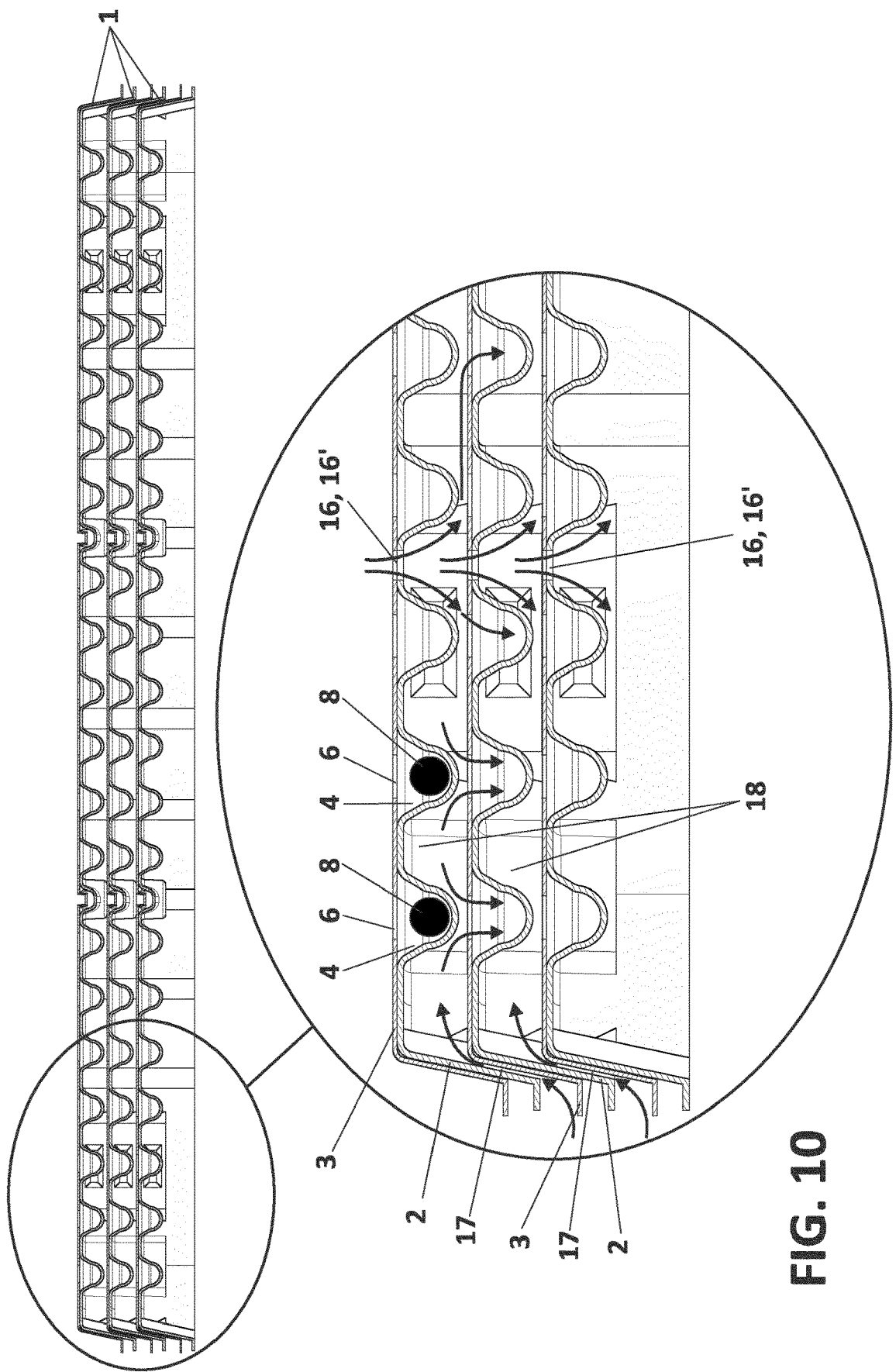
FIG. 10—shows a cross-sectional elevational view of several stacked containers, and an enlarged detail of the containers wherein the air circulation between stacked containers is indicated by arrows.

The lid (3) has a flat surface (7) with a plurality of openings (6) that are arranged in correspondence with the position of the wells (4) in the tray, so when the tray (2) and the lid (3) are coupled together, the lid (3) partially close the wells (4) enclosing the pupae, and each well (4) is accessible through an opening (6), as shown for instance in FIG. 10.

Figure 4:
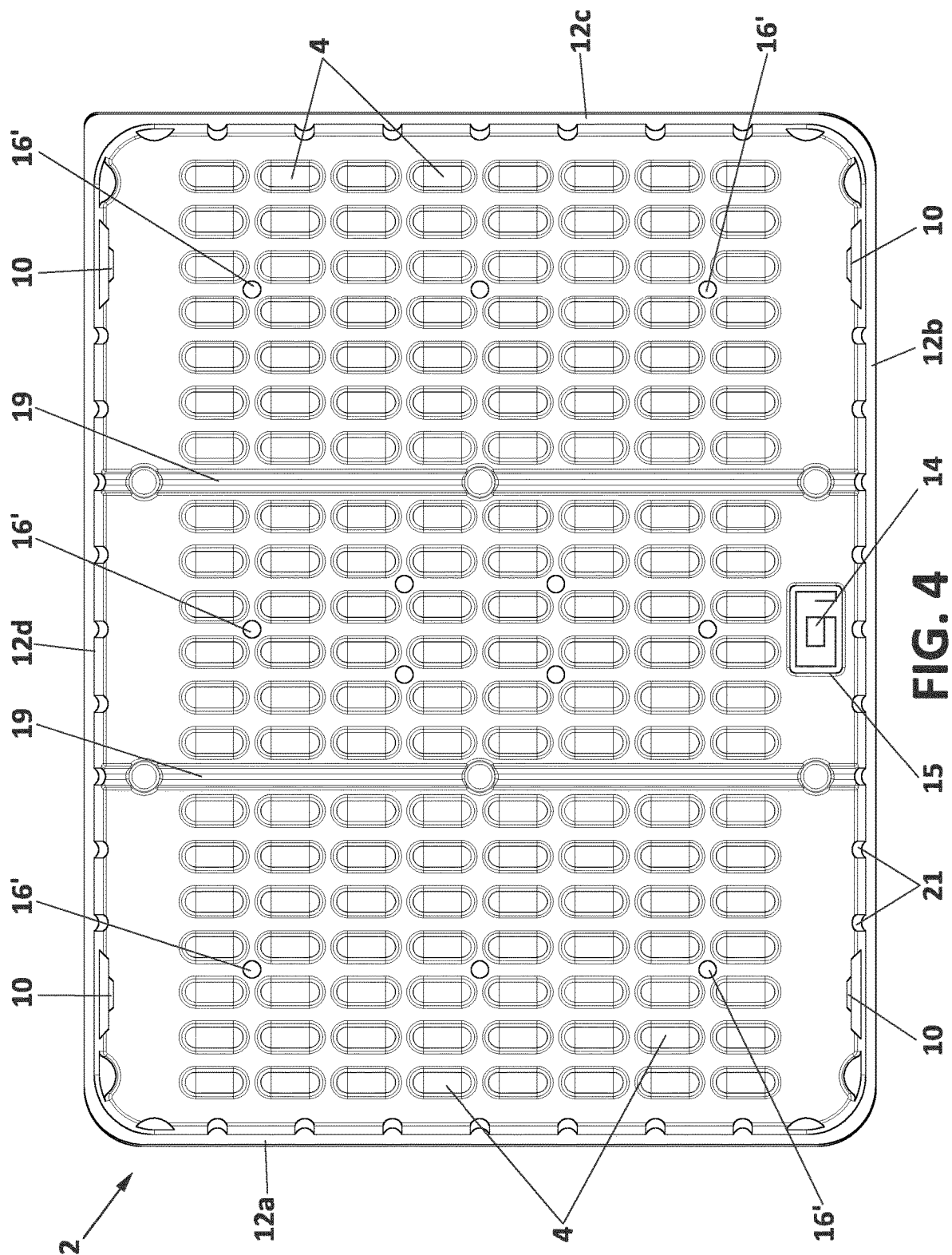
FIG. 4—shows a top plan view of the tray.
Figure 8:
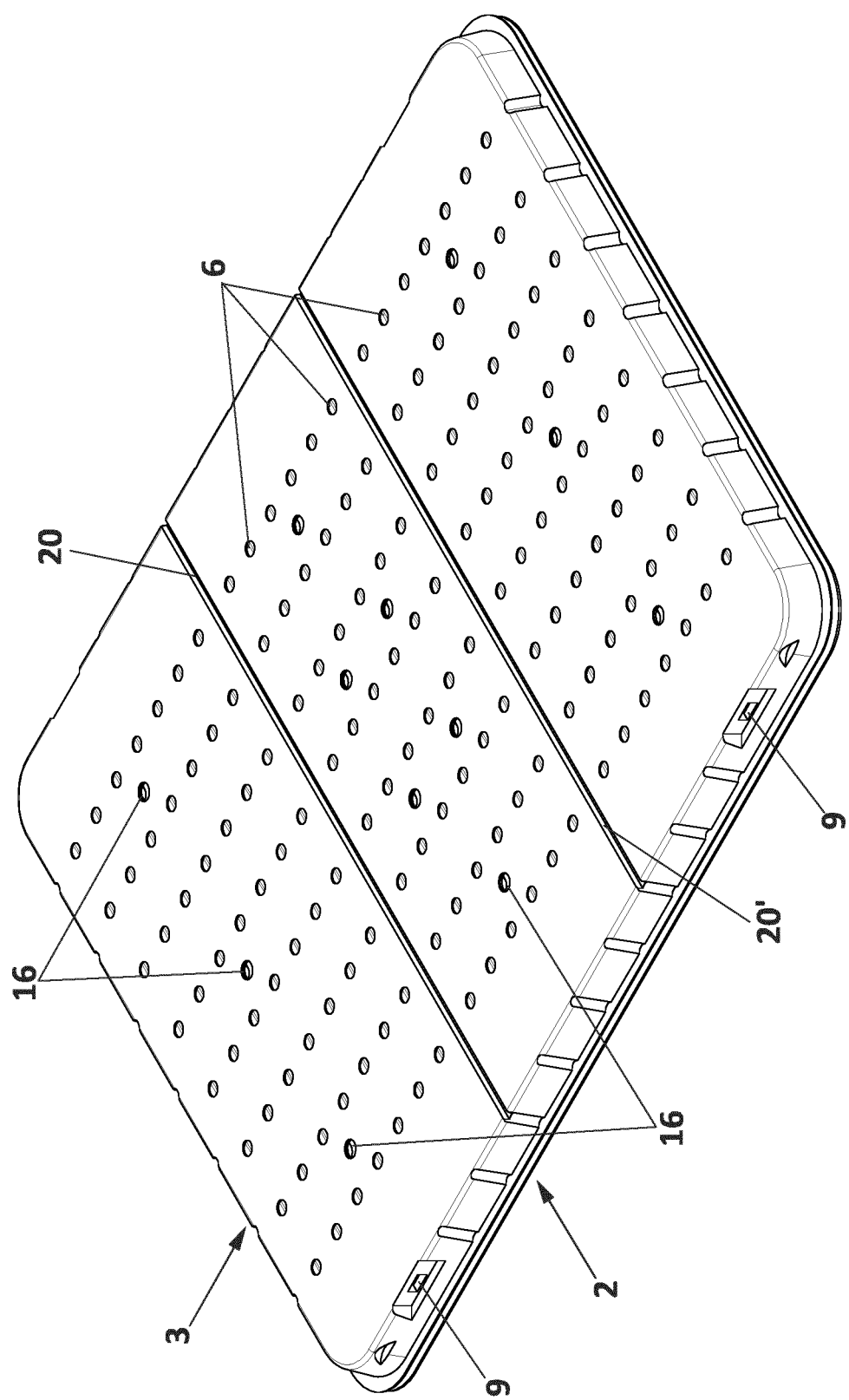
FIG. 8—shows a perspective view of the tray and lid coupled together.
Figure 9:
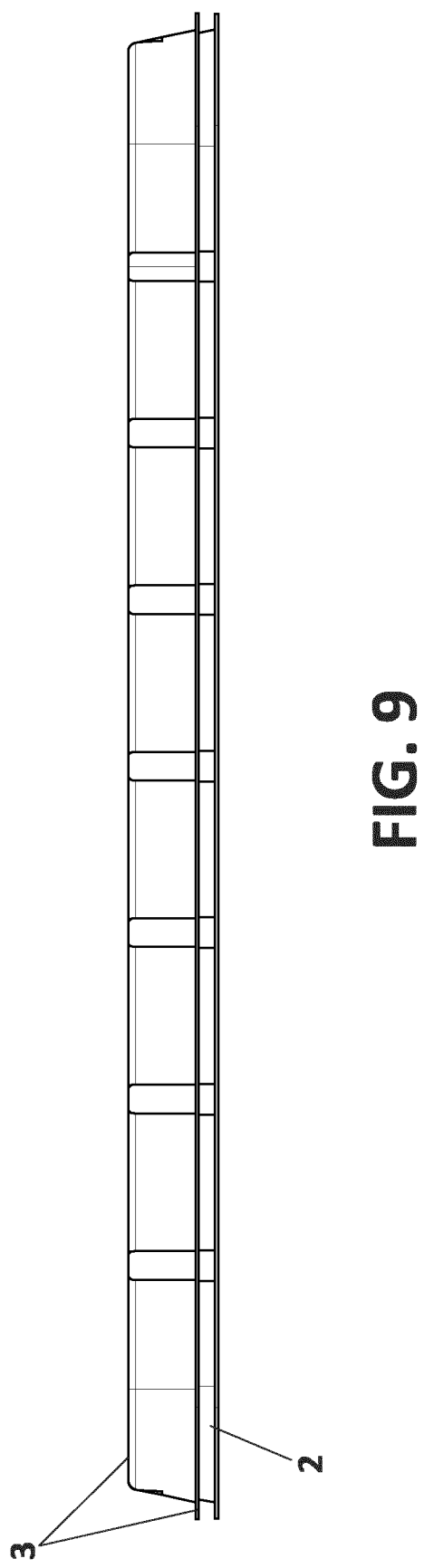
FIG. 9—shows a front elevational view of the tray and lid coupled together.

As shown in FIGS. 4 and 5, preferably the wells (4) and the openings (6) are distributed in columns and rows configuring an orthogonal matrix.

The internal shape of each well (4) is shown in FIGS. 5, 6 and 10. More specifically, each well (4) is an elongated receptacle with generally a frusto-pyramidal configuration, having: a concave bottom surface, an inclined lateral surface and an open upper base. This internal shape of each well (4) has the advantage that a pupa (8) is retained in a fixed position relative to the corresponding opening (6) right over the well (4), through which a needle would be inserted during the inoculation process, thereby preventing any undesired displacement of the pupa (8) while the needle penetrates a pupa.

The tray (2) has a rectangular base (11) defining the flat surface (5) where the wells (4) are formed, and four lateral walls (12a,12b,12c, 12d) respectively at each of the four sides of the base (11), and projecting transversally from the base (11). Similarly, the lid (3) has a rectangular base (21) and four lateral walls (13a, 13b, 13c, 13d) projecting transversally respectively from each of the four sides of the base (21).

Both, the tray (2) and the lid (3) have frusto-pyramidal configuration, shaped and dimensioned to the coupled together as shown for example in FIGS. 6 and 7, so when they are coupled, the bases (5,21) and lateral walls (12a, 13a,12b,13b,12c, 13c, 12d, 13d) overlap.

In order to securely retain the tray and lid engaged during storage and transportation, the tray (2) and the lid (3) are provided with co-operating interlocking means (9, 10) located at the lateral walls (12a,13a,12b,13b, 12c, 13c, 12d, 13d) of the tray (2) and the lid (3). In this preferred embodiment, the interlocking means are configured as male (9) and female (10) snap-fitting members of complementary shape, that are integrally formed respectively with the tray (2) and the lid (3) and provided nearby the four corners of the container (1). For coupling the tray and the lid, these male (9) and female (10) snap-fitting members are pressed together, until the male member (9) engages with the female member (10).

As represented in FIG. 10, the container (1) is configured to be stackable by inserting a top part of a container in the tray of another container.

An air chamber (18) is formed between each pair of consecutive stacked containers (1) fluidly communicated the wells (4) of the same tray (1). The containers (1) are additionally configured to define ventilation passageways (17) between stacked containers (1) as shown in FIG. 10, wherein the ventilation passageways (17) fluidly communicate the air chambers (18) with the exterior environment, so each well (4) is fluidly communicated with the exterior environment through the ventilation passageways (17).

Additionally, additional ventilation passageways comprises overlapping ventilation openings (16, 16') formed in the lid (3) and the tray (2) of the container when a lid and tray are coupled.

Furthermore, the container (1) is provided with an information code containing data and instructions for tracking the pupae incorporated into the container and/or for inoculating the pupae. This code is an electronically, electromagnetically or optically readable code. Preferably, the code is stored in a Radio Frequency Identification (RFID) tag (14) attached to the tray (3), for example glued within a recess (15) formed in the tray (3), and closed by the lid (3), so that the tag (14) is readable through the lid (3). The code preferably include information like: pupae expiration date, inoculation data, tracking number.

The tray and/or the lid include reinforcing means to structurally reinforce the tray and/or the lid respectively. These reinforcement means comprise at least one channel or groove (19, 19') at the base (11) of the tray (2), and at least one channel or groove (20, 20') at the base (21) of the lid (3). The grooves (19, 19', 20, 20') are recessed respectively from base (11) of the tray (2) and the base (21) of the lid (2), and they extend transversally to the tray and lid, and are arranged such as when the tray and the lid are coupled, the grooves (20, 20') of the lid (3) are received inside the grooves (19, 19') of the tray (2) as shown in FIG. 7.

Reinforcing grooves (21, 22) are also formed at the lateral walls (12a,13a,12b,13b,12c, 13c, 12d, 13d) of the tray (2) and the lid (3).

In a preferred embodiment, the tray (2) and the lid (3) are conventionally obtained by thermoforming respective sheet of suitable plastic material.

Figure 11:
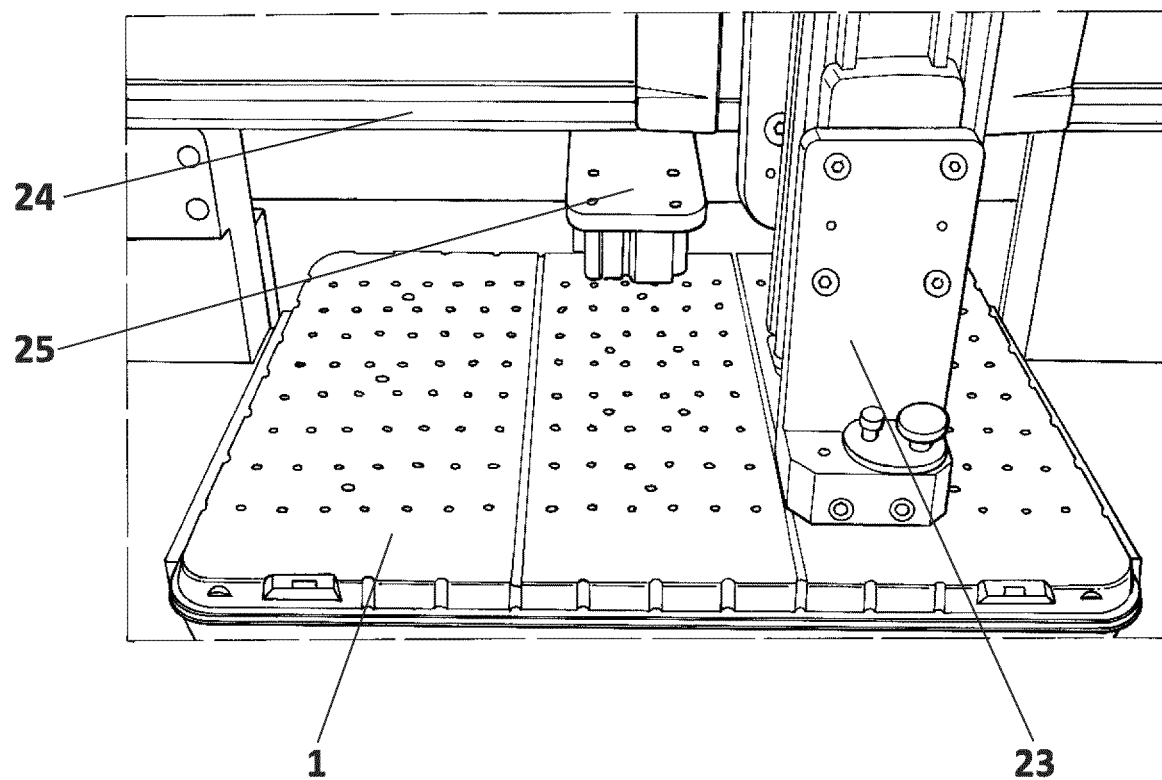
FIG. 11—shows a perspective view of a container in use while it is placed at a compatible baculovirus vector inoculation robot.

FIG. 11 shows a container (1) in use while it is placed at a compatible robot (24) for inoculating the pupae inside the container with a baculovirus vector (1). The inoculation robot (24) includes an inoculation unit (23) that it is displaceable to specific locations according to the matrix distribution of the holes above the pupae, to be inoculated by means of a needle (not shown) installed at the inoculation unit (23). The inoculation unit is connected with a precision pump dispensing the desired volume of the baculovirus vector into the pupae.

The inoculation robot (24) additionally incorporates a reading unit (25) adapted for reading an information code provided in the container (1), in this case a (RFID) tag, so that, the information contained in the code such as: pupae expiration date, inoculation instructions data, and/or container tracking number, is loaded at the inoculation robot (24).

The invention claimed is:

1. A container for transporting and inoculating pupae, comprising:
a tray comprising a flat surface and a plurality of wells formed on the flat surface, each well of the plurality of wells configured for accommodating a pupa; and
a lid having a plurality of openings,
wherein:
the tray comprises a tray base defining the flat surface and comprising four sides, and tray lateral walls transversally projecting from the tray base and extending along the four sides of the tray base, wherein the tray lateral walls comprise a plurality of seats that can engage with a plurality of complementary feet on the lid;
the lid comprises a lid base comprising four sides, and lid lateral walls transversally projecting from the lid base and extending along the four sides of the lid base, wherein the lid lateral walls comprise the plurality of complementary feet that can engage with the plurality of seats on the tray;
the tray and the lid are configured to be coupled to each other such that:
when the tray and the lid are coupled, the tray base and the lid base overlap, and the tray lateral walls and the lid lateral walls overlap, and
when the lid is placed on the flat surface of the tray, the plurality of complementary feet on the lid are supported by the plurality of seats on the tray, and the plurality of the wells are at least partially closed;
the plurality of wells and the plurality of openings are arranged so that when the tray and the lid are coupled together, each well from the plurality of wells is accessible through one of the plurality of openings;
the tray and the lid are provided with interlocking means to mechanically retain the tray and lid engaged;
each well from the plurality of wells is elongated and has generally a frusto-pyramidal configuration with a concave bottom surface, an inclined lateral surface, and an open upper base;
each well from the plurality of wells is configured for retaining one pupa in a fixed position relative to a corresponding opening directly above the well, such that a needle can be inserted through the corresponding opening for inoculating the pupa;
the container is configured as a stackable container such that two or more containers are stackable on top of each other by inserting a top part of a first container from below at least partially in the tray of a second container, wherein in a stacked container:
an interior surface of each of the plurality of seats in the tray of the second container is supported by the flat surface of the first container such that an air chamber is formed between the first container and the second container,
a vertical height of each of the plurality of seats along the tray lateral walls of the second container is such that each of the wells of the second container are situated above the lid of the first container, and each of the wells of the second container are not in contact with a surface of the first container, and
the plurality of wells of the first container are in fluid communication with the air chamber.

2. The container according to claim 1, wherein the container is further configured to define ventilation passageways between stacked containers, and wherein the ventilation passageways are in fluid communication with the air chambers and an exterior environment, wherein each well is in fluid communication with the exterior environment through the ventilation passageways.

3. The container according to claim 1, wherein the ventilation passageways comprise overlapping ventilation openings formed in the lid and the tray of the container and/or wherein the ventilation passageways are formed laterally between the stacked containers.

4. The container according to claim 1, wherein the plurality of wells and the plurality of openings are distributed in columns and rows configuring an orthogonal matrix.

5. The container according to claim 1, wherein the tray and the lid have been obtained by thermoforming a plastic sheet.

6. A set of stacked containers comprising at least two container of claim 1, wherein ventilation passageways are formed laterally between each pair of consecutive stacked containers, and wherein the ventilation passageways are formed by fluid communication of air chambers formed by each pair of consecutive stacked containers.

7. The container according to claim 1, wherein the plurality of wells, the plurality of openings, and the placement of the needle are configured such that the needle penetrates the pupa in the fixed position during the inoculating.

8. The container according to claim 1, wherein: the tray and the lid both have the frusto-pyramidal configuration.

9. The container according to claim 8, wherein the interlocking means are provided at the tray lateral walls and the lid lateral walls, and the interlocking means are configured as male and female snap-fitting members.

10. The container according to claim 1, provided with an information code having information for tracking the container and/or for inoculating the pupae.

11. The container according to claim 10, wherein the information code is an electronically, electromagnetically or optically readable code.

12. The container according to claim 10, further comprising a Radio Frequency Identification (RFID) tag containing the information code.

13. The container according to claim 1, wherein at least one of the tray and the lid include reinforcing means to structurally reinforce the tray, the lid, or combination thereof respectively.

14. The container according to claim 13, wherein:
the reinforcing means comprises at least one groove at a base of the tray and at least one groove at a base of the lid, such that the at least one groove is recessed respectively from the base of the tray and from the base of the lid; and
the at least one groove extends transversally to the tray and lid, and the at least one groove at a base of the tray and at least one groove at a base of the lid are arranged to overlap when the tray and the lid are coupled.

* * * * *